US007006867B1

(12) United States Patent
Kroll

(10) Patent No.: US 7,006,867 B1
(45) Date of Patent: Feb. 28, 2006

(54) METHODS AND APPARATUS FOR OVERDRIVE PACING MULTIPLE ATRIAL SITES USING AN IMPLANTABLE CARDIAC STIMULATION DEVICE

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 617 days.

(21) Appl. No.: 10/192,933

(22) Filed: Jul. 9, 2002

(51) Int. Cl.
*A61N 1/365* (2006.01)

(52) U.S. Cl. .......................................... 607/14; 607/17
(58) Field of Classification Search ................... 607/9, 607/14–15, 17, 25
See application file for complete search history.

(56) References Cited

U.S. PATENT DOCUMENTS

| 5,243,978 | A |   | 9/1993 | Duffin, Jr. ...................... 607/11 |
| 5,713,929 | A |   | 2/1998 | Hess et al. ..................... 607/14 |
| 6,067,469 | A | * | 5/2000 | Kim et al. ...................... 607/4 |
| 6,185,459 | B1 |  | 2/2001 | Mehra et al. ................. 607/14 |
| 6,519,493 | B1 | * | 2/2003 | Florio et al. ................... 607/9 |
| 6,606,517 | B1 | * | 8/2003 | Park et al. ..................... 607/14 |

FOREIGN PATENT DOCUMENTS

| EP | 0607197 B1 | 9/1992 |
| EP | 1110580 A2 | 11/2000 |

OTHER PUBLICATIONS

Chapter 16, "Anti-Tachycardia Pacing and Cardioversion" by Michael L. Hardage and Michael Sweeney in the book "Implantable Cardioverter Defibrillator Therapy," by Mark W. Kroll and Michael H. Lehmann published by Kluwer of Boston in 1996.

* cited by examiner

*Primary Examiner*—Carl Layno

(57) ABSTRACT

Methods and apparatus are disclosed herein that advantageously combine beneficial aspects of overdrive pacing and multi-site atrial pacing in order to provide an improved treatment for atrial fibrillation. The methods and apparatus include sensing of atrial activity at multiple sites within the atria at an overdrive pacing rate to detect intrinsic atrial depolarization, and delivery of pacing pulses to multiple sites within the atria to prevent or terminate arrhythmias such as atrial fibrillation.

18 Claims, 5 Drawing Sheets

METHODS AND APPARATUS FOR OVERDRIVE PACING MULTIPLE ATRIAL SITES USING AN IMPLANTABLE CARDIAC STIMULATION DEVICE

FIELD OF THE INVENTION

The invention generally relates to implantable cardiac stimulation devices such as pacemakers and cardioverter/defibrillators, and in particular, to techniques for overdrive pacing multiple sites within the atria to prevent or terminate chronic arrhythmias, such as paroxysmal atrial fibrillation.

BACKGROUND OF THE INVENTION

Atrial fibrillation is a form of arrhythmia characterized by rapid, uncoordinated and uncontrolled contractions of the atria (the upper chambers of the heart). While typically not fatal, atrial fibrillation keeps the heart from pumping blood efficiently and is a common risk factor for, and cause of, stroke. Atrial fibrillation also markedly diminishes quality of life, and exacerbates heart failure. In the United States, atrial fibrillation presents an immense health care and financial burden, affecting over 2 million people with annual medical expenditures exceeding billions of dollars. The prevalence of atrial fibrillation increases strikingly with advancing age, in that 4% of men and women in the U.S. older than 60 and 10% of those older than 80 suffer from atrial fibrillation.

Traditional approaches to atrial fibrillation treatment centered primarily on pharmacological therapy. A more recent non-pharmacological technique for preventing or terminating arrhythmias is to overdrive pace the heart wherein an implantable cardiac stimulation device, such as a pacemaker, applies electrical pacing pulses to the heart at a rate somewhat faster than the intrinsic heart rate of the patient. To prevent tachyarrhythmias from occurring, the cardiac stimulation device artificially paces the heart at a rate of, generally, five to ten pulses per minute faster than the intrinsic heart rate of the patient. This technique is often referred to as Dynamic Overdrive Pacing or DAO. In other words, a slight artificial tachycardia is induced and maintained in an effort to prevent an actual tachycardia from arising. If an actual tachycardia occurs, the cardiac stimulation device senses the tachycardia and immediately begins pacing with short bursts at a rate of about 10–20% faster than the tachycardia in an effort to capture the heart and thereby terminate the tachycardia. This technique is often referred to as Anti-Tachycardia Pacing or ATP.

It is believed that overdrive pacing is effective for at least some patients for preventing the onset of an actual tachycardia for several reasons. A normal, healthy heart beats only in response to electrical pulses generated from a portion of the heart referred to as the sinus node. The sinus node pulses are conducted to the various atria and ventricles of the heart via certain, normal conduction pathways. In some patients, however, additional portions of the heart also generate electrical pulses referred to as "ectopic" pulses. Each pulse, whether a sinus node pulse or an ectopic pulse has a refractory period subsequent thereto during which time the heart tissue is not responsive to any electrical pulses. A combination of sinus pulses and ectopic pulses can result in a dispersion of the refractory periods, which, in turn, can trigger a tachycardia. By overdrive pacing the heart at a uniform rate, the likelihood of the occurrence of ectopic pulses is reduced and the refractory periods within the heart tissue are rendered uniform and periodic. Thus, the dispersion of refractory periods is reduced and tachycardias triggered thereby are substantially avoided.

It is therefore desirable within patients prone to tachyarrhythmias to ensure that most beats of the heart are paced beats, as any unpaced beats may be ectopic beats. A high percentage of paced beats can be achieved simply by establishing a high overdrive-pacing rate. But, a high overdrive-pacing rate is disadvantageous in that it may be unpleasant to the patient, particularly if the artificially induced heart rate is relatively high in comparison with the heart rate that would otherwise normally occur. A high heart rate may also cause possible damage to the heart or may possibly trigger more serious dysrhythmias, such as a ventricular fibrillation. A high overdrive-pacing rate may be especially problematic in patients suffering from heart failure, particularly if the heart failure is due to an impaired diastolic function. A high overdrive-pacing rate may actually exacerbate heart failure in these patients. Also, a high overdrive-pacing rate may be a problem in patients with coronary artery disease because increasing the heart rate decreases diastolic time and decreases perfusion, thus intensifying ischemia. Also, the need to apply overdrive-pacing pulses operates to deplete the implantable cardiac stimulation device's internal power supply, perhaps requiring frequent surgical replacement of the power supply.

In view of these concerns, a desirable approach to overdrive pacing is to reduce the average overdrive-pacing rate, while still attaining a sufficiently high rate to significantly reduce the likelihood of a dysrhythmia within the patient or to terminate a dysrhythmia if one nevertheless occurs. Such an overdrive pacing technique permits a certain percentage of paced beats (such as 90% or 95%) to be sustained by the cardiac stimulation device so as to enable the overdrive pacing rate to be minimized while ensuring that most beats of the heart are paced beats. An example of an overdrive pacing system that operates in this manner to reduce the likelihood of a dysrhythmia within a patient, or terminate a dysrhythmia altogether, is provided by U.S. patent application Ser. No. 09/471,788, for "Methods and Apparatus for Overdrive Pacing Heart Tissue Using an Implantable Cardiac Stimulation Device," incorporated by reference herein.

Another approach to treatment of arrhythmias is to pace within multiple sites of the atria. Such multi-site atrial pacing has been used to suppress atrial fibrillation in patients with sinus node disease or that have been rendered bradycardiac by antiarrhythmic drugs used to maintain sinus rhythm. Some studies also suggest that multi-site pacing is an effective method of preventing paroxysmal atrial fibrillation by increasing cardiac performance through electrical resynchronization. It would therefore be desirable to provide techniques that combine beneficial aspects of overdrive pacing and multi-site atrial pacing in order to provide improved treatment for atrial fibrillation. It is to this end that aspects of the present invention are primarily directed.

SUMMARY

In accordance with the teachings of the present invention, methods and apparatus are disclosed herein that advantageously combine beneficial aspects of overdrive pacing and multi-site atrial pacing in order to provide an improved treatment for atrial fibrillation. The methods and apparatus include sensing of atrial activity at multiple sites within the atria to detect intrinsic atrial depolarization, and delivery of pacing pulses to multiple sites within the atria to prevent or terminate arrhythmias such as atrial fibrillation.

More particularly, an exemplary implantable medical device comprises a plurality of leads adapted to be disposed within an atrium of a heart, a sensing system adapted to sense atrial activity through at least one of the plurality of leads, a pulse generator adapted to deliver atrial pacing pulses to the atrium through at least one of the plurality of leads at an overdrive pacing rate, and a control system, operatively coupled to the sensing system and pulse generator, that determines the overdrive pacing rate based in part on the sensed atrial activity. The plurality of leads may further comprise a first lead adapted to be coupled to the interatrial septum of the atrium, a second lead adapted to be coupled to the sinus node of the right atrium, and a third lead adapted to be coupled to the left atrium through the coronary sinus/great vein of the patient's heart.

The implantable medical device of the present invention permits multiple site sensing and/or multiple site pacing in various different ways that may be selected by a physician to provide a customized treatment for a patient. In one embodiment of the invention, the sensing system may be adapted to sense the atrial activity through one of the plurality of leads, and the pulse generator is further adapted to deliver atrial pacing pulses though a different one of the plurality of leads. In another embodiment of the invention, the sensing system may be adapted to sense the atrial activity through a corresponding one of the plurality of leads that first detects the atrial activity. In yet another embodiment of the invention, the pulse generator may be further adapted to deliver the atrial pacing pulses in a staggered manner, with a first pulse delivered to a first one of the plurality of leads and a second pulse delivered to a second one of the plurality of leads, and with a predetermined time delay defined between delivery of the first and second pulses.

A method for overdrive pacing a patient's heart using an implantable cardiac stimulation device connected to the heart comprises the steps of disposing a plurality of leads within an atrium of the heart, sensing atrial activity through at least one of the plurality of leads, determining an overdrive pacing rate based in part on the sensed atrial activity, and delivering atrial pacing pulses to the atrium through at least one of the plurality of leads at the overdrive pacing rate. A first one of the plurality of leads may be coupled to the interatrial septum of the atrium, a second one of the plurality of leads may be coupled to the sinus node of the atrium, and a third one of the plurality of leads may be coupled to the left atrium through the coronary sinus/great vein of the patient's heart.

More particularly, the method includes multiple site sensing and/or multiple site pacing. In one embodiment, the method further comprises sensing the atrial activity through one of the plurality of leads, and delivering the atrial pacing pulses though a different one of the plurality of leads. In another embodiment, the method comprises sensing through a corresponding one of the plurality of leads that first detects the atrial activity. In yet another embodiment, the delivering step further comprises delivering the atrial pacing pulses in a staggered manner, with a first pulse delivered to a first one of the plurality of leads and a second pulse delivered to a second one of the plurality of leads, and with a predetermined time delay defined between delivery of the first and second pulses. The delivering step may additionally comprise delivering the first pulse having a first energy level and the second pulse having a second energy level, wherein the first energy level is different from the second energy level.

A more complete understanding of the method and apparatus for overdrive pacing multiple atrial sites using an implantable cardiac stimulation device will be afforded to those skilled in the art, as well as a realization of additional advantages and objects thereof, by a consideration of the following detailed description of the preferred embodiment. Reference will be made to the appended sheets of drawings, which will first be described briefly.

DETAILED DESCRIPTION

The present invention satisfies the need for techniques that combine beneficial aspects of overdrive pacing and multi-site atrial pacing to provide an improved treatment for atrial fibrillation. As will be further described below, the invention relates to techniques for controlling overdrive pacing delivered to multiple sites within the right and left atria so as to achieve and maintain a target degree of pacing. In the detailed description that follows, like element numerals are used to describe like elements illustrated in one or more of the figures.

Figure 1:
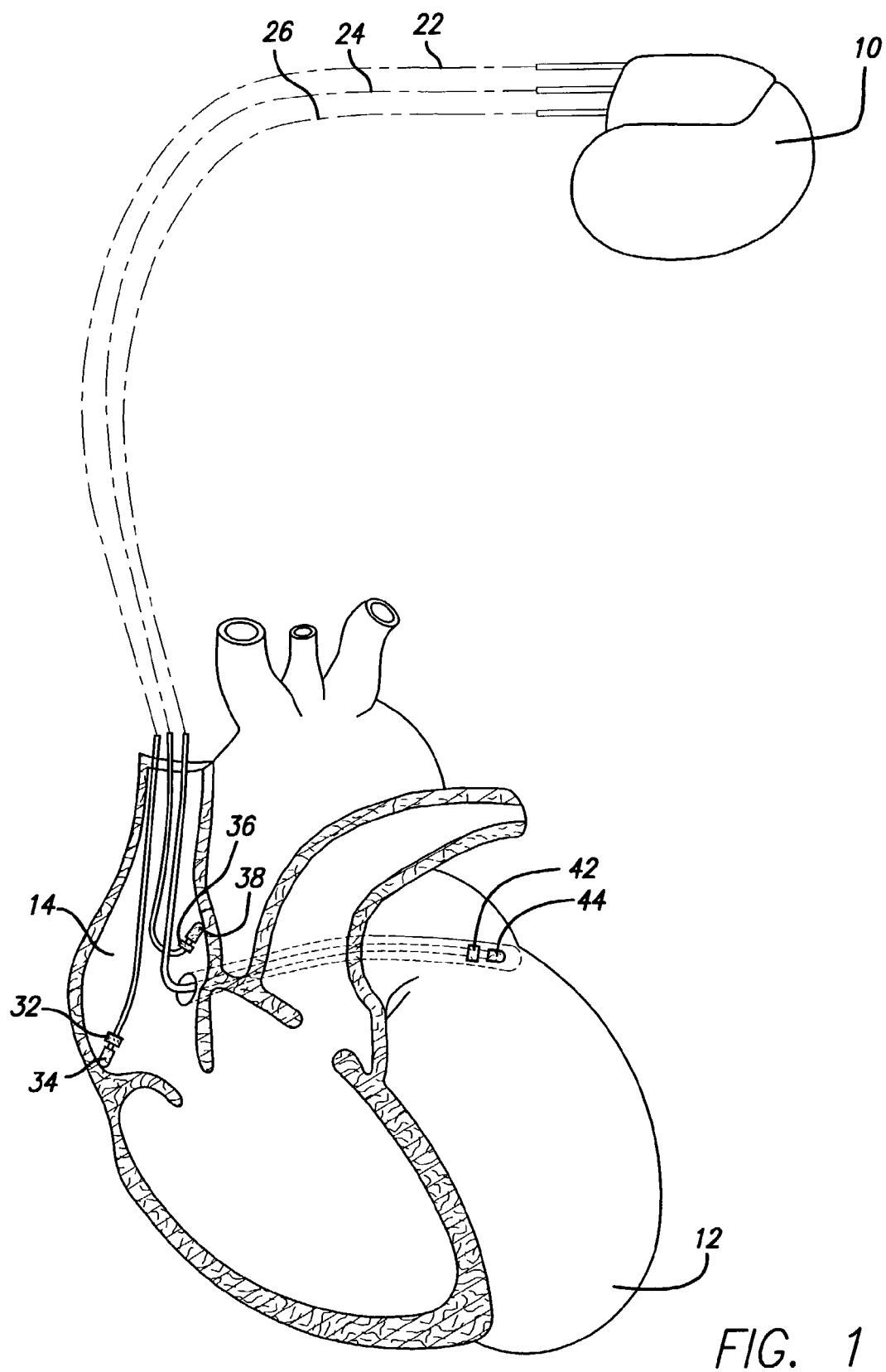
FIG. 1 is a schematic diagram illustrating a pacemaker connected to a patient's heart to provide multi-site atrial sensing and pacing.

Referring first to FIG. 1, an implantable cardiac stimulating device 10 (such as a pacemaker) is coupled to a patient's heart 12 by way of a plurality of atrial leads, including a first atrial lead 22, a second atrial lead 24, and a third atrial lead 26. The first atrial lead 22 includes a tip electrode 34 and ring electrode 32 positioned in a first portion of the right atrium 14 of the heart 12 corresponding to the sinus node (preferably using a screw-in active fixation lead). The second atrial lead 24 includes a tip electrode 36 and a ring electrode 38 positioned in a second portion of the right atrium 14 of the heart 12 corresponding to the interatrial septum (also preferably using a screw-in active fixation lead). The third atrial lead 26 includes a tip electrode 42 and a ring electrode 44 positioned adjacent to the left atrium, within the coronary sinus/great vein of the patient's heart 12. As will be further described below, the third atrial lead 26 may not be included in all embodiments of the present invention.

Various internal components of the pacemaker operate to sense the electrical activity of the heart 12, such as the presence of P-waves, using electrode pairs 34/32, 36/38, and 42/44 and to selectively stimulate the heart in response to events sensed within the heart 12 by conducting electrical stimulation pulses to the heart 12 using the electrode pairs. Among other functions, the pacemaker operates to overdrive pace the heart 12 in accordance with techniques to be described below in an effort to prevent the occurrence of a tachycardia or, if a tachycardia nevertheless occurs, to terminate the tachycardia. It should be appreciated that the implantable cardiac device may also include additional leads and/or electrodes, such as leads adapted to provide ventricular pacing and/or shocking coil electrodes adapted to deliver cardioversion shocking pulses. These and aspects of the implantable cardiac device unrelated to the present invention are omitted from this description in the interest of simplification.

Figure 2:
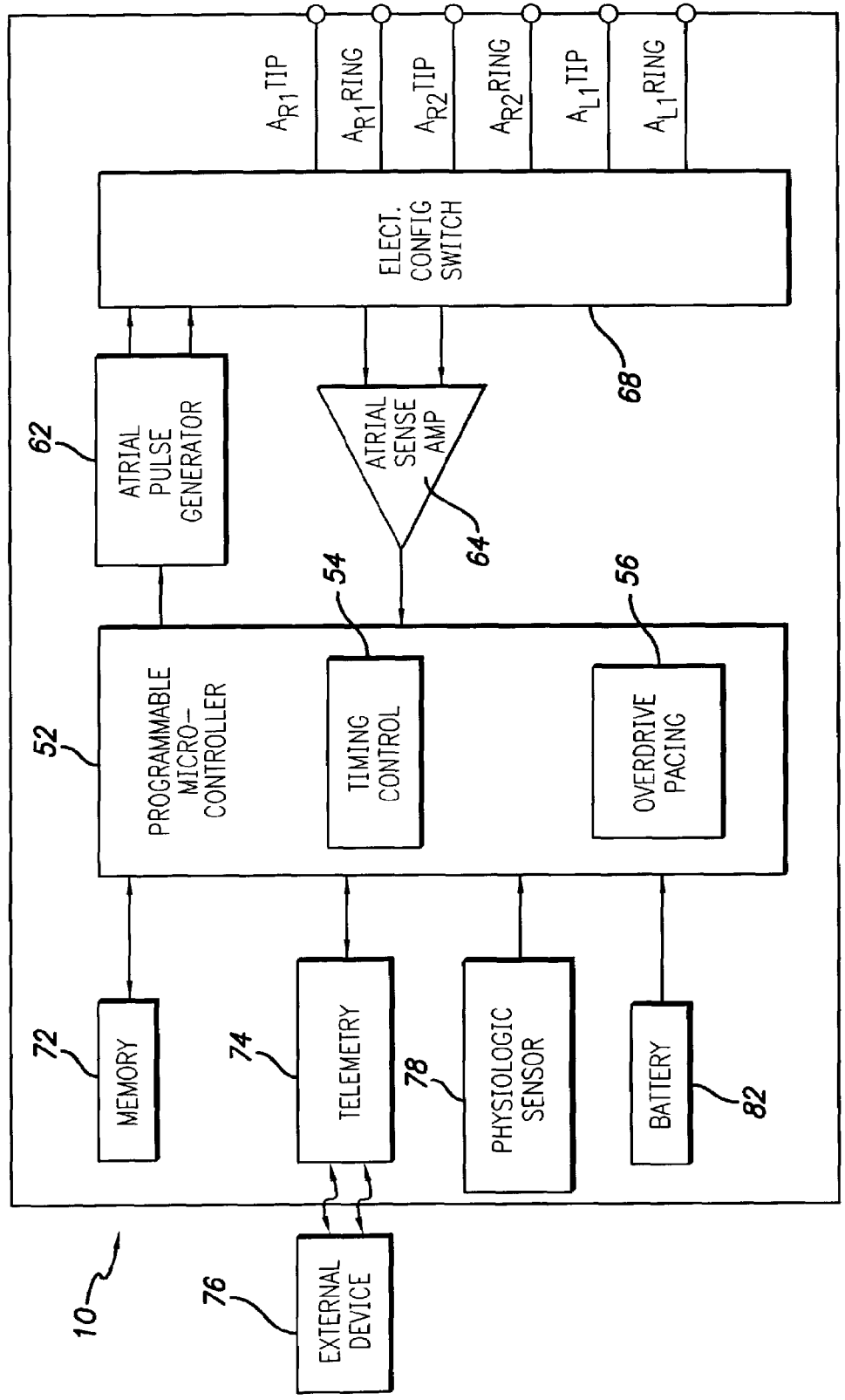
FIG. 2 is a block diagram of a pacemaker in accordance with an embodiment of the invention.

FIG. 2 sets forth a simplified block diagram of an embodiment of the implantable cardiac stimulation device 10. The cardiac stimulation device 10 includes within an enclosure a programmable microcontroller 52, an atrial pulse generator circuit 62, an atrial sense amplifier 64, and an electrically configurable switch 68. The electrically configurable switch 68 includes three pairs of electrical connectors labeled as $AR_1$ tip/ring, $AR_2$ tip/ring, and $A_{L1}$ tip/ring that are adapted to be connected to the aforementioned first, second, and third atrial leads 22, 24, 26, respectively. The cardiac stimulation device 10 is controlled by the programmable microcontroller 52 to carry out the control and timing functions in accordance with stored algorithms. The microcontroller 52 may be provided by a conventional microprocessor, digital signal processor, programmable logic device, application specific integrated circuit, or the like. The microcontroller 52 receives output signals from the atrial sense amplifier 64 and generates trigger signals that are sent to the atrial pulse generator 62. The electrically configurable switch 68 is controlled by the microcontroller 52 to enable interconnection of any of the atrial leads 22, 24, 26 to the atrial pulse generator 62 and the atrial sense amplifier 64, depending upon an operating mode of the cardiac stimulation device 10 as described below. This way, any one or more of the atrial leads 22, 24, 26 may carry stimulating pulses from the atrial pulse generator 62 to a corresponding portion of the right and/or left atria. Similarly, electrical signals from the atrium may be carried via one of more of the atrial leads 22, 24, 26 to the atrial sense amplifier 64.

The cardiac stimulation device 10 also includes a memory 72 that is connected to the microcontroller 52 over a suitable data/address bus. The memory 72 allows certain control parameters, used by the microcontroller 52 in controlling the operation of the cardiac stimulation device 10, to be stored and modified, as required, in order to customize the operation of the stimulation device to the needs of a particular patient. The cardiac stimulation device 10 also includes a telemetry communications circuit 74 that is connected to the microcontroller 52 by way of a suitable command/data bus. In turn, the telemetry circuit 74 is selectively coupled to an external programming device 76 by an appropriate communication link such as any suitable electromagnetic link. Advantageously, desired commands may be sent from the external programming device to the microcontroller 52. Other data measured within or by the stimulation device 10 may be stored in the memory 72 and uploaded to the external programming device 76.

The cardiac stimulation device 10 also includes a physiological sensor 78 that is connected to the microcontroller 52 over a suitable connection line. In the preferred embodiment, the physiological sensor 78 detects patient activity via an accelerometer, but could alternatively be any appropriate sensor that can indicate patient activity. In addition, any sensor that indicates metabolic need over time could be used in place of the activity sensor, such as an oxygen saturation sensor, temperature sensor, etc. Lastly, the cardiac stimulation device 10 additionally includes a battery 82 that provides operating power to all the circuits of the stimulation device via a power signal line.

The microcontroller 52 is adapted to control operation of the cardiac stimulation device 10 by executing algorithms in the form of embedded or stored instructions. The algorithms include a timing control algorithm 54 and an overdrive-pacing algorithm 56. The timing control algorithm 54 determines the timing of operation of the cardiac stimulation device 10 based on detected atrial events. The overdrive-pacing algorithm 56 is intended to generate overdrive-pacing pulses at a sufficiently high rate to minimize the number of unpaced beats without causing an unnecessarily high heart rate. In an embodiment of the invention, the cardiac stimulation device 10 determines the actual degree of pacing resulting from the overdrive pacing pulses and adaptively modifies the overdrive-pacing rate to maintain the actual degree of pacing at about a target degree of pacing wherein about 95% of the total beats are paced beats. The cardiac stimulation device 10 also controls the delivery of overdrive pacing pulses to multiple sites within the atria in order to further reduce or terminate an arrhythmia such as atrial fibrillation. It should be appreciated that or more of these algorithms may be implemented as an electronic circuit rather than as stored instructions. Moreover, other algorithms adapted to perform different functions may also be included in the cardiac stimulation device 10.

Figure 3:
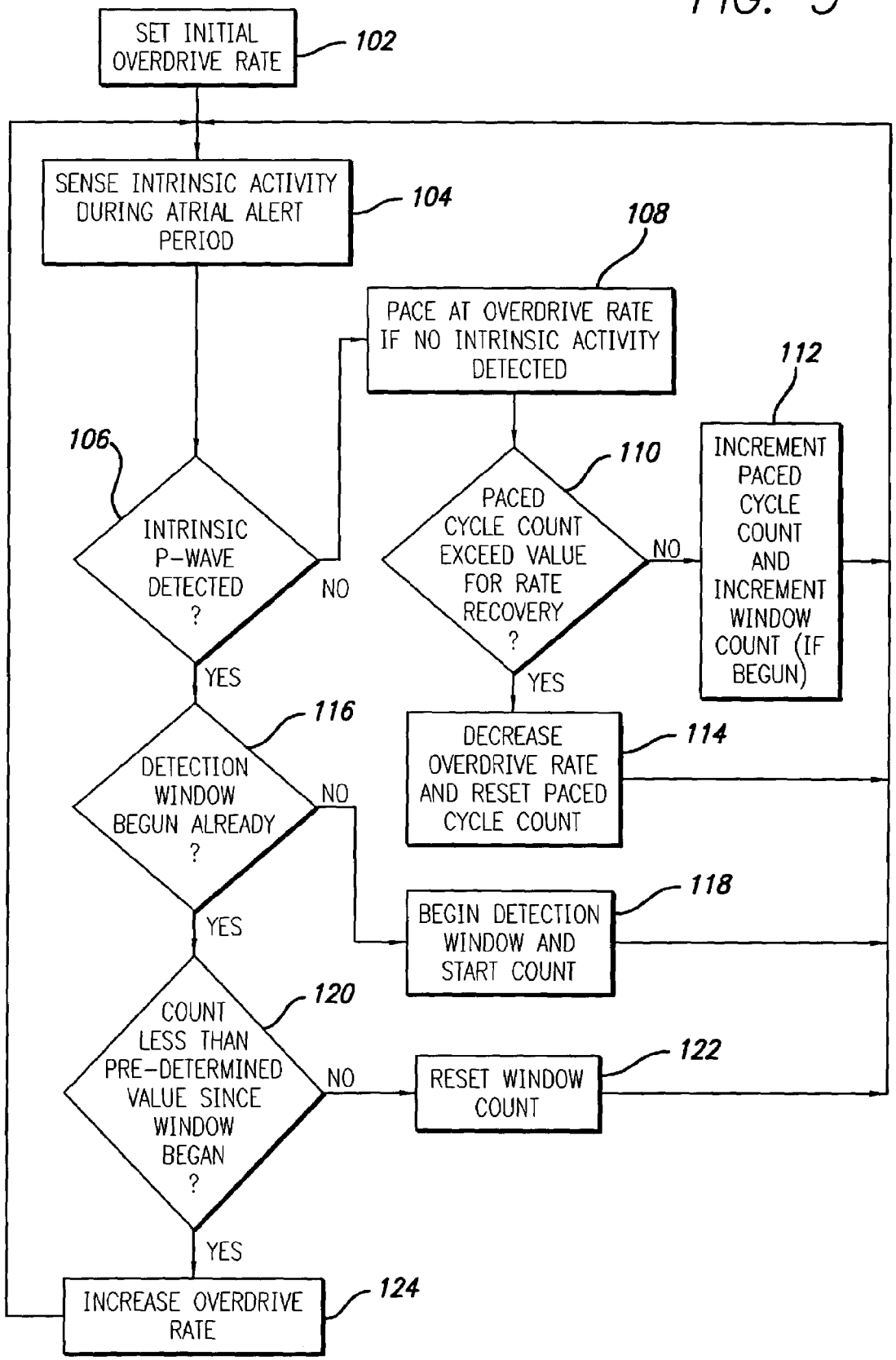
FIG. 3 is a flow chart illustrating an embodiment of an overdrive-pacing algorithm.

FIG. 3 is a flow chart illustrating one technique for implementing an overdrive pacing algorithm which, among other features (1) increases an overdrive pacing rate if two P-waves are detected within a predetermined number of cardiac cycles of one another, and (2) decreases the overdrive pacing rate if a rate increase does not occur within a predetermined number of cardiac cycles. In another embodiment of the overdrive pacing algorithm, the overdrive pacing rate is periodically reset to be equal to a detected sinus rate every predetermined number of cardiac cycles regardless of the extent to which the overdrive pacing rate is modified during the interim.

Initially, at step 102, a current overdrive pacing rate is set, such as to be equal to the detected sinus rate. Following this step, a loop begins that repeats with every atrial cycle, during which the overdrive pacing rate may be increased or decreased depending upon detected intrinsic atrial activity, as will be further described below. The algorithm may periodically return to step 102 (not shown) to redefine the baseline overdrive-pacing rate, such as by monitoring the intrinsic atrial sinus rate. As known in the art, an atrial cycle includes a refractory period and an alert period. The atrial refractory period begins with an atrial sensed or paced event. During the refractory period, the atrial sense amplifier 64 is unresponsive to intrinsic signals by operation of the electrically configurable switch 68, as will be further described below. The alert period follows the refractory period and ends with the next sensed or paced event. During the atrial alert period, the atrial sense amplifier 64 can sense intrinsic cardiac activity, once again by operation of the electrically configurable switch 68. If intrinsic atrial activity is not sensed during the atrial alert period, the atrial pulse generator 62 will deliver an atrial pulse at the rate determined by the overdrive pacing algorithm or other programmable mode to one or more sites within the atria.

More particularly, at step 104, the cardiac stimulation device 10 senses intrinsic atrial activity during an atrial alert period. As will be further described below, the cardiac stimulation device 10 may sense intrinsic atrial activity from a single atrial site, or multiple atrial sites. At step 106, a determination is made as to whether an intrinsic P-wave was detected during the atrial alert period. If no intrinsic P-wave was detected, the cardiac stimulation device 10 delivers a pacing pulse at step 108 at the current overdrive-pacing rate. Atrial pacing may be applied to a single atrial site, or multiple atrial sites, as will also be described below. The steps that follow step determine whether the current overdrive rate should be increased or decreased.

If at step 106 it was determined that an intrinsic P-wave was detected during the atrial alert period, then the overdrive pacing algorithm determines whether it is appropriate to increase the overdrive pacing rate. In an embodiment of the invention, a single detected P-wave is not sufficient to trigger an increase in the overdrive-pacing rate. This is because a single detected P-wave may not reflect the onset of paroxysmal atrial fibrillation, and it preferable to increase the overdrive-pacing rate only when there is a greater likelihood that atrial fibrillation is present. To accomplish this, a preferred embodiment of the overdrive-pacing algorithm looks for plural intrinsic P-waves occurring within a predetermined number of atrial cycles. Alternatively, it should also be appreciated that the present invention is not limited to this preferred embodiment, and increases in the overdrive rate could follow the detection of a single detected P-wave.

The detection of a first intrinsic P-wave initiates the start of a detection window that lasts for a predetermined number of atrial cycles. If a second intrinsic P-wave is detected during the detection window, the overdrive-pacing rate is increased. In step 116, the overdrive-pacing algorithm determines whether a detection window has begun already (indicating that a first intrinsic P-wave has already been detected). If a detection window has not yet begun, then the algorithm passes to step 118 in which the detection window is begun and a count of atrial cycles within the window is started. The algorithm then returns to step 104 to await the start of the next atrial alert period. But, if a detection window has already begun, then the algorithm passes to step 120 in which the algorithm determines whether the count of atrial cycles within the detection window is less than a predetermined value. The predetermined value determines the time length of the detection window. In a preferred embodiment of the invention, the predetermined value is sixteen atrial cycles, although it should be appreciated that other values could be advantageously utilized. If the count of atrial cycles since the last detected intrinsic P-wave is less than the predetermined value, indicating the possible onset of paroxysmal atrial fibrillation, then at step 124 the overdrive-pacing rate is increased. The algorithm then returns to step 104 to await the start of the next atrial alert period. Conversely, if the count of atrial cycles since the last detected intrinsic P-wave is not less than the predetermined value, the count of atrial cycles within the detection window is reset, essentially starting a new detection window. The algorithm then returns to step 104 to await the start of the next atrial alert period without increasing the overdrive-pacing rate.

Returning to step 106, if it was determined that an intrinsic P-wave was not detected during the atrial alert period, and the atria was paced at the current overdrive rate at step 108, the overdrive pacing algorithm determines whether to begin rate recovery, i.e., reduction of the overdrive pacing rate. If a sufficient number of paced atrial cycles occurs without further increases to the overdrive-pacing rate, then rate recovery can begin. At step 110, the algorithm determines whether a count of paced atrial cycles exceeds a predetermined value to permit rate recovery. In a preferred embodiment of the invention, the predetermined value is sixteen paced atrial cycles, although it should be appreciated that other values could be advantageously utilized. If the paced cycle count exceeds the predetermined value, then the overdrive rate is decreased at step 114 and the paced cycle count reset to zero. The algorithm then returns to step 104 to await the start of the next atrial alert period. Alternatively, if the paced cycle count does not exceed the predetermined value, then the paced cycle count is incremented at step 112. Also, if the detection window had been previously begun at step 118, the count of atrial cycles since the last detected intrinsic P-wave is also incremented. The algorithm then returns to step 104 to await the start of the next atrial alert period.

In the event that the detected rate of the heart is very high, such as over 180 PPM, then the steps of the foregoing paragraphs may be replaced by an ATP approach. According to this approach, the pacing therapy is a burst of approximately eight to fifteen pulses, each at a rate roughly 10–20% higher than the detected rate. An example of an ATP algorithm can be found in Chapter 16, "Anti-Tachycardia Pacing and Cardioversion" by Michael L. Hardage and Michael Sweeney in the book "Implantable Cardioverter Defibrillator Therapy," by Mark W. Kroll and Michael H. Lehmann published by Kluwer of Boston in 1996, incorporated by reference herein.

Figure 4:
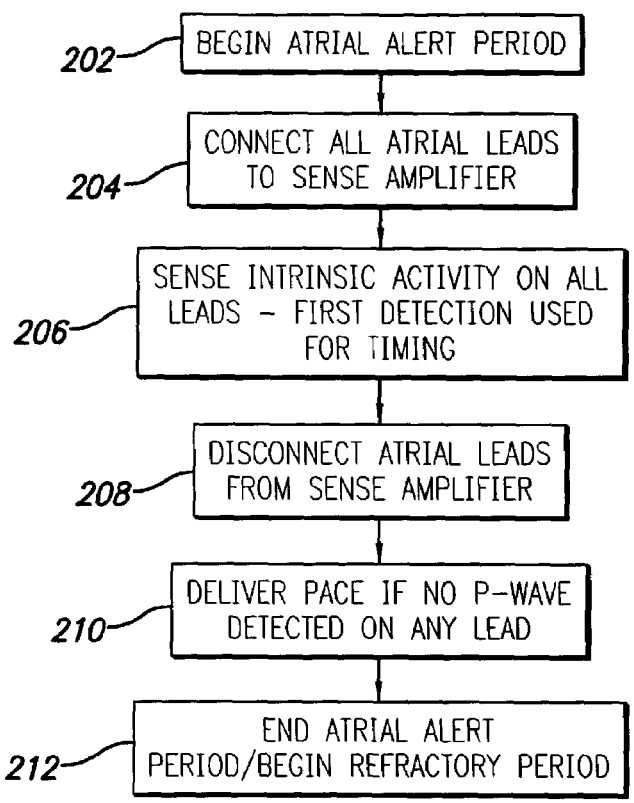
FIG. 4 is a flow chart illustrating a multi-site sensing algorithm in accordance with an embodiment of the invention.
Figure 5:
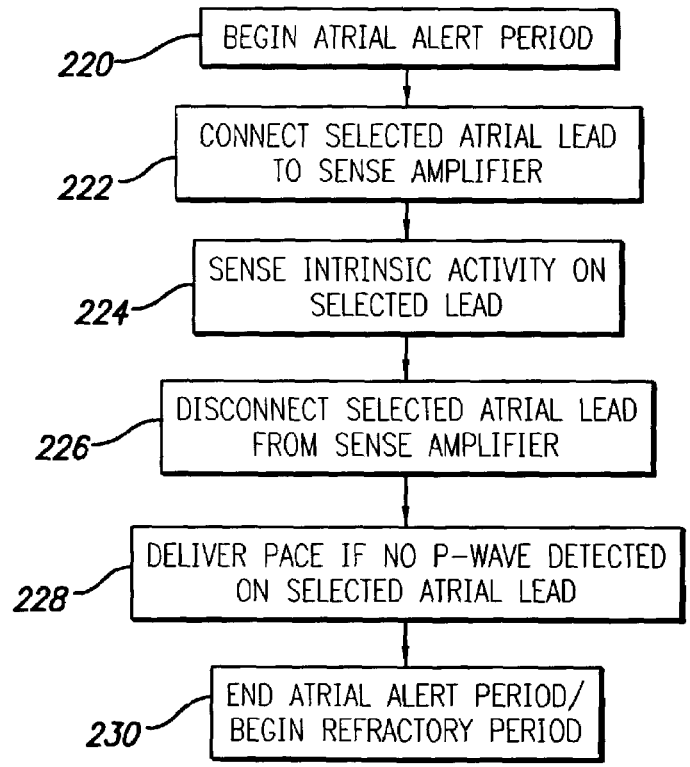
FIG. 5 is a flow chart illustrating a multi-site sensing algorithm in accordance with another embodiment of the invention.

As described above, the timing control algorithm 54 determines the timing of operation of the cardiac stimulation device 10 based on detected atrial events. In an embodiment of the invention, the timing control algorithm 54 further determines the timing of multiple site atrial sensing operations and multiple site atrial pacing operations of the cardiac stimulation device 10 in conjunction with operation of the overdrive-pacing algorithm 56. FIGS. 4 and 5 further illustrate exemplary multiple site atrial sensing algorithms, and FIGS. 6 and 7 further illustrate exemplary multiple site atrial pacing algorithms, which are each described in further detail below. It should be appreciated that the multiple site atrial sensing algorithms correspond generally to step 104 described above with respect to FIG. 3, and the multiple site atrial pacing algorithms correspond generally to step 108 described above with respect to FIG. 3.

FIG. 4 is a block diagram illustrating an embodiment of a multiple site atrial sensing algorithm. In this embodiment, intrinsic activity of the atria is sensed at multiple sites using all of the atrial leads (e.g., leads 22, 24, 26 of FIG. 1). At step 202, the atrial alert period begins following a preceding refractory period of a cardiac cycle. Next, at step 204, all of the atrial leads are connected to the atrial sense amplifier 64 by operation of the electrically configurable switch 68. This enables intrinsic atrial activity to be sensed through each of the leads in parallel at step 206. The atrial sense amplifier 64 provides an electrical signal to the programmable microcontroller 52 that can be used to detect a P-wave. Thereafter, in step 208, the atrial leads are disconnected from the atrial sense amplifier 64 by operation of the electrically configurable switch 68. If a P-wave was not detected on any of the atrial leads during the atrial alert period, a pacing pulse is delivered to the atria at step 210 (delivery of pacing pulses to multiple atrial sites is described below). Lastly, at step 212, the atrial alert period ends and the next refractory period begins.

An intrinsic atrial depolarization ordinarily begins at the atrial sinus node and then propagates through the surrounding cardiac tissue to other portions of the atria. It would therefore be expected that atrial lead 22 having electrode pair 32, 34 disposed at the atrial sinus node would detect the depolarization earlier than the other atrial leads 24, 26 disposed more distant from the sinus node. But, depending upon the physical condition of the patient's atria, the depolarization may in some cases be detected first in other portions of the atria instead of at the sinus node. In a preferred embodiment of the invention, the atrial-sensing algorithm would utilize the first detection of a depolarization for purpose of determining timing of the atrial alert and refractory periods. Alternatively, the atrial sensing algorithm could be adapted to utilize the last detection of a depolarization for this purpose, or an average or extrapolation between the first and last detections. It is further anticipated that first detection, last detection, and other such combinations thereof be defined as parameters that a physician can select upon implantation of the cardiac stimulation device 10 or during later reprogramming of the device so as to customize operation of the cardiac stimulation device to a patient.

FIG. 5 is a block diagram illustrating another embodiment of a multiple site atrial sensing algorithm. In this embodiment, intrinsic activity of the atria is sensed at a selected site using one of multiple atrial leads. At step 220, the atrial alert period begins following a preceding refractory period of a cardiac cycle. Next, at step 222, a selected atrial lead is connected to the atrial sense amplifier 64 by operation of the electrically configurable switch 68. This enables intrinsic atrial activity to be sensed through the selected lead at step 224. Thereafter, in step 226, the selected atrial lead is disconnected from the atrial sense amplifier 64 by operation of the electrically configurable switch 68. If a P-wave was not detected on the selected atrial lead during the atrial alert period, a pacing pulse is delivered to the atria at step 228 (described below). Lastly, at step 230, the atrial alert period ends and the next refractory period begins.

As described above, an intrinsic atrial depolarization ordinarily begins at the atrial sinus node and then propagates through the surrounding cardiac tissue to other portions of the atria. It may therefore be preferable to sense only through the atrial lead disposed closest to the atrial sinus node (e.g., lead 22), rather than through all of the leads as in the previous embodiment. Or, depending upon the physical condition of the atria and the location of the other leads, it may be preferred to sense another one of the leads disposed elsewhere within the atria. This embodiment permits the physician to select one of the atrial leads for sensing intrinsic atrial activity. It is anticipated that this selection be a programmable mode that may be selected by the physician to customize operation of the cardiac stimulation device 10 to the patient.

Figure 6:
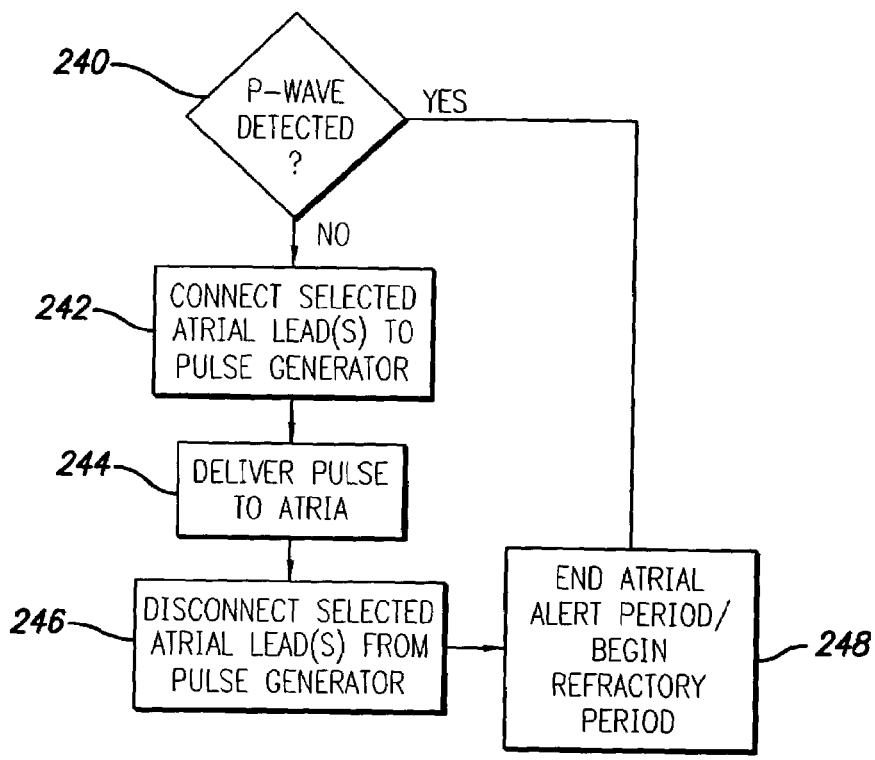
FIG. 6 is a flow chart illustrating a multi-site pacing algorithm in accordance with an embodiment of the invention.

FIG. 6 is a block diagram illustrating an embodiment of a multiple site atrial pacing algorithm. In this embodiment, the cardiac stimulation device 10 delivers pacing pulses to a selected site within the atria using one of multiple atrial leads. At step 240, the pacing algorithm determines whether a P-wave was detected during the atrial alert period, such as using one of the foregoing embodiments of the invention. If a P-wave was detected, the atrial alert period ends and the next refractory period begins at step 248. But, if a P-wave was not detected, the algorithm passes to step 242 in which a selected atrial lead is connected to the atrial pulse generator 62 by operation of the electrically configurable switch 68. This enables a pacing pulse to be delivered to a selected site within the atria through the selected lead at step 244. Thereafter, in step 246, the selected atrial lead is disconnected from the atrial pulse generator 62 by operation of the electrically configurable switch 68. Lastly, at step 248, the atrial alert period ends and the next refractory period begins.

Some clinical data suggests that pacing on the interatrial septum can be advantageous in preventing atrial fibrillation. It would therefore be desirable to deliver pacing pulses through atrial lead 24 having electrode pair 36, 38 disposed at the interatrial septum instead of the other atrial leads 22, 26 disposed more distant from the interatrial septum. But, depending upon the physical condition of the patient's atria, it may be preferable to deliver pacing pulses to other portions of the atria instead of at the interatrial septum. Or, it may alternatively be preferred to deliver pacing pulses to multiple locations simultaneously, such as to both the interatrial septum and the region adjacent to the left atrium within the coronary sinus/great vein of the patient's heart. This embodiment allows the selection of a specific region or regions for delivery of pacing pulses. It is further anticipated that a particular lead or leads be defined as parameters that a physician can select upon implantation of the cardiac stimulation device 10 or during later reprogramming of the device so as to customize operation of the cardiac stimulation device to a patient.

Figure 7:
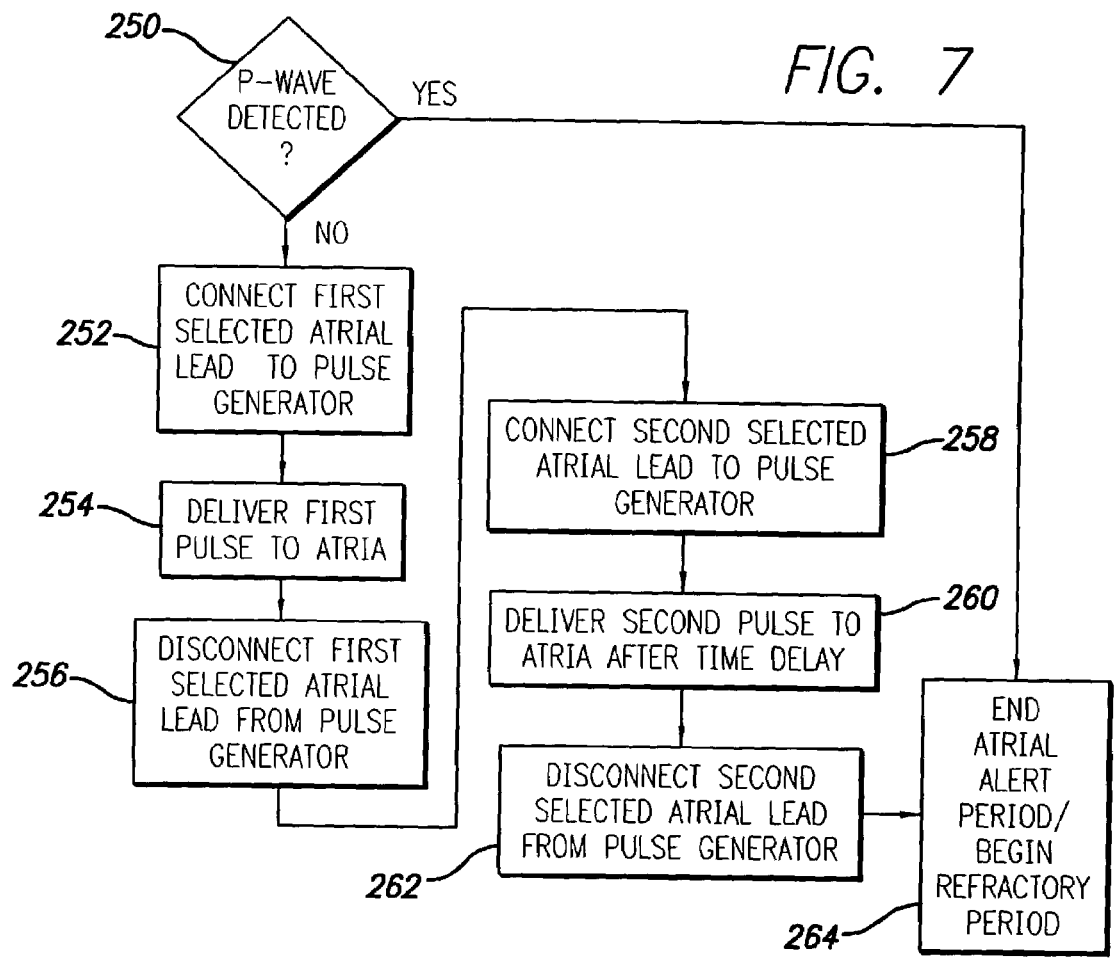
FIG. 7 is a flow chart illustrating a multi-site pacing algorithm in accordance with another embodiment of the invention.

FIG. 7 is a block diagram illustrating another embodiment of a multiple site atrial pacing algorithm. In this embodiment, the cardiac stimulation device 10 delivers pacing pulses in a staggered manner in which a first pacing pulse is delivered to a selected site and a second pacing pulse is delivered to another site after a time delay. At step 250, the pacing algorithm determines whether a P-wave was detected during the atrial alert period. If a P-wave was detected, the atrial alert period ends and the next refractory period begins at step 264. But, if a P-wave was not detected, the algorithm passes to step 252 in which a first selected atrial lead is connected to the atrial pulse generator 62 by operation of the electrically configurable switch 68. This enables a first pacing pulse to be delivered to a selected site within the atria through the selected lead at step 254. Then, in step 256, the first selected atrial lead is disconnected from the atrial pulse generator 62 by operation of the electrically configurable switch 68. Next, in step 258, a second selected atrial lead is connected to the atrial pulse generator 62 by operation of the electrically configurable switch 68. This enables a second pacing pulse to be delivered to another selected site within the atria through the selected lead at step 260. The second pacing pulse may be delayed in time from the first pacing pulse by a predetermined time period, such as twelve milliseconds. Then, in step 262, the second selected atrial lead is disconnected from the atrial pulse generator 62 by operation of the electrically configurable switch 68. Lastly, at step 264, the atrial alert period ends and the next refractory period begins.

As discussed above, a natural atrial depolarization begins at the sinus node and propagates through the cardiac tissue to the rest of the atria. Accordingly, the staggered delivery of pacing pulses would simulate the natural progression of a depolarization. It would therefore be desirable to deliver a first pacing pulse through atrial lead 22 having electrode pair 32, 34 disposed at the sinus node, and a second pacing pulse through atrial lead 24 having electrode pair 36, 38 disposed at the interatrial septum after a time delay corresponding to the time it would ordinarily take for the depolarization energy to propagate that distance (e.g., twelve milliseconds). Depending upon the physical condition of the patient's atria, it may be preferable to deliver the first pacing pulse to another portion of the atria instead of the sinus node. Or, it may alternatively be preferred to deliver the second pacing pulses simultaneously to both the interatrial septum and to the region adjacent to the left atrium within the coronary sinus/great vein of the patient's heart. Moreover, the amount of pacing energy delivered in the first pacing pulse can differ from that delivered in the second pacing pulse. This embodiment allows the selection of specific regions for delivery of pacing pulses, as well as the order of pacing pulse delivery, the duration of the time delay, and the magnitude of the pacing pulse. It is further anticipated that each of these parameters be selectable by a physician upon implantation of the cardiac stimulation device 10 or during later reprogramming of the device so as to customize operation of the cardiac stimulation device to a patient.

It is anticipated that that the foregoing algorithms be combined to provide unique and/or optimized treatment for a patient. For example, it may be desirable to sense intrinsic atrial activity at one location (e.g., the atrial sinus node) using the embodiment of FIG. 5, and deliver pacing pulses to another location (e.g., the interatrial septum) using the embodiment of FIG. 6. Or, it may be desirable to utilize multiple site atrial sensing using the embodiment of FIG. 4 with multiple site delayed pacing using the embodiment of FIG. 7. It should be appreciated by persons having ordinary skill in the art that other combinations of the embodiments may also be advantageously utilized within the scope of the present invention.

Having thus described a preferred embodiment of a method and apparatus for overdrive pacing multiple atrial sites using an implantable cardiac stimulation device, it should be apparent to those skilled in the art that certain advantages of the described method and apparatus have been achieved. It should also be appreciated that various modifications, adaptations, and alternative embodiments thereof may be made within the scope and spirit of the present invention. For example, in an alternative embodiment of the invention, two or more atrial leads could be connected to the atrial sense amplifier 64 and/or the atrial pulse generator 62 using a conventional bifurcated connector. This would enable cardiac stimulation devices already not configured for multiple site atrial sensing and/or pacing to provide some of the aforementioned functions. A drawback of this alternative embodiment is that it does not permit reprogramming by physician to change the characteristics of the multiple site atrial sensing and/or pacing to accommodate changes in patient physiology.

The invention is further defined by the following claims.

What is claimed is:

1. An implantable medical device comprising:
   a plurality of leads adapted to be disposed within an atrium of a heart;
   a sensing system adapted to sense atrial activity through one of the plurality of leads;
   a pulse generator adapted to deliver atrial pacing pulses to the atrium through a different one of the plurality of leads at an overdrive pacing rate; and
   a control system, operatively coupled to the sensing system and pulse generator, that determines the overdrive-pacing rate based in part on the sensed atrial activity;
   wherein the plurality of leads comprise a first lead adapted to be coupled to the interatrial septum of the atrium; and
   wherein the plurality of leads comprise a second lead adapted to be coupled to the sinus node of the right atrium.

2. The implantable medical device of claim 1, wherein the plurality of leads comprise a third lead adapted to be coupled to the left atrium through the coronary sinus of the patient's heart.

3. The implantable medical device of claim 2, wherein the third lead comprises a bipolar lead.

4. The implantable medical device of claim 1, wherein the sensing system is adapted to sense the atrial activity through a corresponding one of the plurality of leads that first detects the atrial activity.

5. The implantable medical device of claim 1, wherein the sensing system is adapted to permit selection of one of the plurality of leads for detection of the atrial activity.

6. The implantable medical device of claim 1, wherein the pulse generator is adapted to permit selection of one of the plurality of leads for delivery of the atrial pacing pulses.

7. An implantable medical device comprising:
   a plurality of leads adapted to be disposed within an atrium of a heart;
   a sensing system adapted to sense atrial activity through one of the plurality of leads;
   a pulse generator adapted to deliver atrial pacing pulses to the atrium through a different one of the plurality of leads at an overdrive pacing rate; and
   a control system, operatively coupled to the sensing system and pulse generator, that determines the overdrive-pacing rate based in part on the sensed atrial activity;
   wherein the pulse generator is further adapted to deliver the atrial pacing pulses in a staggered manner, with a first pulse delivered to a first one of the plurality of leads and a second pulse delivered to a second one of the plurality of leads, and with a predetermined time delay defined between delivery of the first and second pulses; and
   wherein the predetermined time delay is approximately 12 milliseconds.

8. The implantable medical device of claim 7, wherein the first one of the plurality of leads is coupled to the sinus node of the atrium and the second one of the plurality of leads is coupled to the interatrial septum of the atrium.

9. An implantable medical device comprising:
   a plurality of leads adapted to be disclosed within an atrium of a heart;
   a sensing system adapted to sense atrial activity through one of the plurality of leads;
   a pulse generator adapted to deliver atrial pacing pulses to the atrium through a different one of the plurality of leads at an overdrive pacing rate; and
   a control system, operatively coupled to the sensing system and pulse generator, that determines the overdrive-pacing rate based in part on the sensed atrial activity;
   wherein the pulse generator is further adapted to deliver the atrial pacing pulses in a staggered manner, with a first pulse delivered to a first one of the plurality of leads and a second pulse delivered to a second one of the plurality of leads, and with a predetermined time delay defined between delivery of the first and second pulses; and
   wherein the first pacing pulse and the second pacing pulse deliver different amounts of energy.

10. A method for overdrive pacing a patient's heart using an implantable cardiac stimulation device connected to the heart, the method comprising;
   disposing a plurality of leads within an atrium of the heart;
   sensing atrial activity through at least one of the plurality of leads;
   determining an overdrive pacing rate based in part on the sensed atrial activity; and
   delivering atrial pacing pulses to the atrium through at least one of the plurality of leads at the overdrive-pacing rate, wherein the at least one of the plurality of leads used to deliver the atrial pacing pulses is different from the at least one of the plurality of leads used to sense atrial activity;

wherein the disposing step further comprises coupling a first one of the plurality of leads to the interatrial septum of the atrium; and wherein the disposing step further comprises coupling a second one of the plurality of leads to the sinus node of the atrium.

11. The method of claim 10, wherein the sensing step further comprises sensing through a corresponding one of the plurality of leads that first detects the atrial activity.

12. The method of claim 10, wherein the sensing step further comprises selecting one of the plurality of leads for detection of the atrial activity.

13. The method of claim 10, wherein the delivering step further comprises selecting one of the plurality of leads for delivery of the atrial pacing pulses.

14. The method of claim 10, wherein the determining step further comprises determining said overdrive pacing rate in accordance with a dynamic overdrive algorithm to prevent an arrhythmic condition of the atrium.

15. The method of claim 10, wherein the determining step further comprises determining said overdrive pacing rate in accordance with an anti-tachycardia pacing algorithm to terminate an arrhythmic condition of the atrium.

16. A method of overdrive pacing a patient's heart using an implantable cardiac stimulation device connected to the heart, the method comprising:

disposing a plurality of leads within an atrium of the heart;

sensing atrial activity through at least one of the plurality of leads;

determining an overdrive pacing rate based in part on the sensed atrial activity; and delivering atrial pacing pulses to the atrium through at least one of the plurality of leads at the overdrive-pacing rate, wherein the at least one of the plurality of leads used to deliver the atrial pacing pulses is different from the at least one of the plurality of leads used to sense atrial activity;

wherein the delivering step further comprises delivering the atrial pacing pulses in a staggered manner, with a first pulse delivered to a first one of the plurality of leads and a second pulse delivered to a second one of the plurality of leads, and with a predetermined time delay defined between delivery of the first and second pulses; and wherein the delivering step further comprises delivering the first pulse having a first energy level and the second pulse having a second energy level, wherein the first energy level is different from the second energy level.

17. A method for overdrive pacing a patient's heart using an implantable cardiac stimulation device connected to the heart, the method comprising:

disposing a plurality of leads within an atrium of the heart;

sensing atrial activity through at least one of the plurality of leads;

determining an overdrive pacing rate based in Part on the sensed atrial activity; and delivering atrial pacing pulses to the atrium through at least one of the plurality of leads at the overdrive-pacing rate, wherein the at least one of the plurality of leads used to deliver the atrial pacing pulses is different from the at least one of the plurality of leads used to sense atrial activity;

wherein the delivering step further comprises delivering the atrial pacing pulses in a staggered manner, with a first pulse delivered to a first one of the plurality of leads and a second pulse delivered to a second one of the plurality of leads, and with a predetermined time delay defined between delivery of the first and second pulses; and wherein the predetermined time delay is approximately 12 milliseconds.

18. The method of claim 17, wherein the disposing step further comprises coupling the first one of the plurality of leads to the sinus node of the atrium and coupling the second one of the plurality of leads to the interatrial septum of the atrium.

* * * * *